(12) United States Patent
Bowden

(10) Patent No.: US 10,588,334 B2
(45) Date of Patent: Mar. 17, 2020

(54) SYSTEM AND METHODS FOR SUPERCOOLING PERISHABLE PRODUCTS

(71) Applicant: The Bowden Group, Honolulu, HI (US)

(72) Inventor: R. Craig Bowden, Honolulu, HI (US)

(73) Assignee: RLMB Group, LLC, Honolulu, HI (US)

( * ) Notice: Subject to any disclaimer, the term of this patent is extended or adjusted under 35 U.S.C. 154(b) by 51 days.

(21) Appl. No.: 15/815,296

(22) Filed: Nov. 16, 2017

(65) Prior Publication Data

US 2019/0142037 A1    May 16, 2019

(51) Int. Cl.
| | |
|---|---|
| *A23L 3/26* | (2006.01) |
| *A23L 3/32* | (2006.01) |
| *A23L 3/36* | (2006.01) |
| *A23L 3/365* | (2006.01) |
| *A01N 1/02* | (2006.01) |

(52) U.S. Cl.
CPC .................. *A23L 3/26* (2013.01); *A23L 3/32* (2013.01); *A23L 3/362* (2013.01); *A23L 3/364* (2013.01); *A23L 3/365* (2013.01); *A01N 1/0252* (2013.01); *A01N 1/0284* (2013.01); *A23V 2002/00* (2013.01)

(58) Field of Classification Search
CPC ............ A23L 3/32; A23L 3/26; A01N 1/0252
See application file for complete search history.

(56) References Cited

U.S. PATENT DOCUMENTS

| | | | |
|---|---|---|---|
| 4,367,630 A * | 1/1983 | Bernard ................. | A23B 4/062 62/63 |
| 5,084,377 A | 1/1992 | Rowan et al. | |
| 2008/0160496 A1 | 7/2008 | Rzepakovsky et al. | |
| 2011/0000231 A1 * | 1/2011 | McCormick .............. | A23L 3/30 62/63 |
| 2015/0147778 A1 | 5/2015 | Pickard | |
| 2016/0108484 A1 | 4/2016 | Preston et al. | |

OTHER PUBLICATIONS

International Search Report and Written Opinion in related International Application No. PCT/US2018/061614, dated Jan. 25, 2019 (9 pages).

* cited by examiner

*Primary Examiner* — Sean E Conley
(74) *Attorney, Agent, or Firm* — Venable LLP; Michele V. Frank

(57) ABSTRACT

A system for supercooling a product is provided, the system comprising: a chamber containing a supercooling medium; and disruptors that emit sound waves, ultrasound waves, and/or electromagnetic waves in the chamber; wherein during a cooling cycle the chamber reaches a cooling temperature below 0° C. and during a warming cycle the chamber reaches a warming temperature greater than the cooling temperature. The supercooling system may be used to supercool perishable products below freezing to extend shelf life and freshness of the products. Other embodiments of the supercooling system, and methods for its use, are described herein.

22 Claims, 2 Drawing Sheets

SYSTEM AND METHODS FOR SUPERCOOLING PERISHABLE PRODUCTS

TECHNICAL FIELD

The present invention generally relates to and describes methods and systems of super cooling of products. More specifically, embodiments of the present invention relate to using a low temperature cooling process to improve shelf-life, and the targeted use of energy including sound waves, ultrasonic frequencies, and electromagnetic energy to disrupt the formation of ice crystals and impede the negative effects of low temperature cooling in perishable products.

BACKGROUND

Fresh produce offers many quality, nutritional, and perceived benefits over cooked or otherwise processed foods. However, fresh foods are perishable products with short shelf lives that undergo senescence, or the natural aging and gradual deterioration process, and they are highly susceptible to pathogens. Perishable products must therefore be maintained in a lower temperature environment to slow this aging process and to retard the growth of spoilage pathogenic organisms. Lowering the temperature leads to increased shelf life and higher quality without cooking or drying the product, and without using chemicals, or extremely high pressures for preservation. The lower the temperature, the more the internal metabolic processes that causes senescence are slowed, or even stopped. However, lowering the temperature to at or below freezing may cause tissue damage to the product so that it is no longer in its desired fresh or natural state. Freezing may damage the texture and negatively affect product integrity and nutritional profile.

Current methods of cooling perishable products use several different techniques these include, for example, immersion, forced air cooling, hydro-cooling, and vacuum cooling.

Forced air cooling, whereby air is drawn across the product, may take several hours to cool the products. Thus, it is less effective at slowing senescence. Furthermore, the product packaging requires sufficient venting for core product temperatures to be uniformly reduced to optimum levels.

Hydro-cooling utilizes cold water to drench the product. This process takes less time to cool the products and is more efficient than forced air cooling but is not appropriate for all perishable products, especially where direct water contact has a negative impact on product quality making it less than the ideal solution for many products.

Vacuum cooling whereby air is withdrawn from a sealed chamber lowering the boiling point, facilitates evaporative cooling and may cause rapid cooling of the product (additional refrigeration is often added to further speed this process). This process is relatively fast but takes a very large amount of energy to cool the products, and is not appropriate for cooling many perishables that cannot withstand the negative pressure experienced during this process.

Although all of these various cooling methods (including other commercial cooling methods not described) have a use for some products and some circumstances, all these processes fail in their ability to further benefit the product and/or further slow the metabolic processes. In addition, at a point where ice crystals or product freezing occurs the potential benefits from cooling in all of these processes are replaced by negative impact of product damage. Once the product's cells are damaged from chilling injury, or more typically freezing and no longer frozen, these products are even more susceptible to degradation, spoilage, and pathogenic organisms.

The thermal transfer of heat energy from perishable products and organisms effectively "decreases" the metabolic rate/respiration slowing biological processes and senescence, in the case of produce this decrease generally occurs in a manner proportional to the Q10 decrease in temperature. As the products, spoilage and/or other living organisms' temperature approaches freezing, biological processes slow but more energy is required for each proportional decrease in temperature. Once a product or organism reaches its freezing point, the negative effects from a further decrease in temperature can only be managed by creating a targeted and controlled disruption/prevention of ice crystals and undesirable reactions that lead to cellular damage. The use of targeted energy transfer to a product within a controlled environment can reduce the chance for damage due to freezing by using waves of certain frequency prior to, during, and immediately after a product is cooled to or below its normal freezing temperature. The result is a product whose metabolic processes have been slowed or nearly stopped for a time and when this technique is combined with other carefully applied good handling practices it will allow that product to have a longer shelf-life than other fresh or perishable products that were not supercooled.

Therefore, there is a need in the art for systems and methods of supercooling perishable products that overcome the foregoing and other drawbacks of the prior art.

SUMMARY

According to an embodiment, a method for supercooling a product is provided, the method comprising: surrounding a perishable product in a supercooling medium until the product reaches a core temperature of below 0° C.; disrupting the formation of ice crystals within the product while in the supercooling medium using sound waves, ultrasound waves, or electromagnetic waves individually or in combinations; and warming the product to a warming temperature ranging from just below freezing to above freezing.

According to another embodiment, a system for supercooling a product is provided, the system comprising: a chamber containing a supercooling medium; and disruptors that emit sound waves, ultrasonic waves, and/or electromagnetic waves into the chamber containing the product; wherein during a cooling cycle the chamber reaches a temperature below 0° C. and during a warming cycle the chamber reaches a temperature above 0° C.

BRIEF DESCRIPTION OF THE DRAWINGS

The features and advantages of the invention will be apparent from the following drawings wherein like reference numbers generally indicate identical, functionally similar, and/or structurally similar elements.

DETAILED DESCRIPTION

Embodiments of the invention are discussed in detail below. In describing embodiments, specific terminology is employed for the sake of clarity. A person skilled in the relevant art will recognize that other equivalent parts can be employed and other methods developed without departing from the spirit and scope of the invention.

Figure 1:
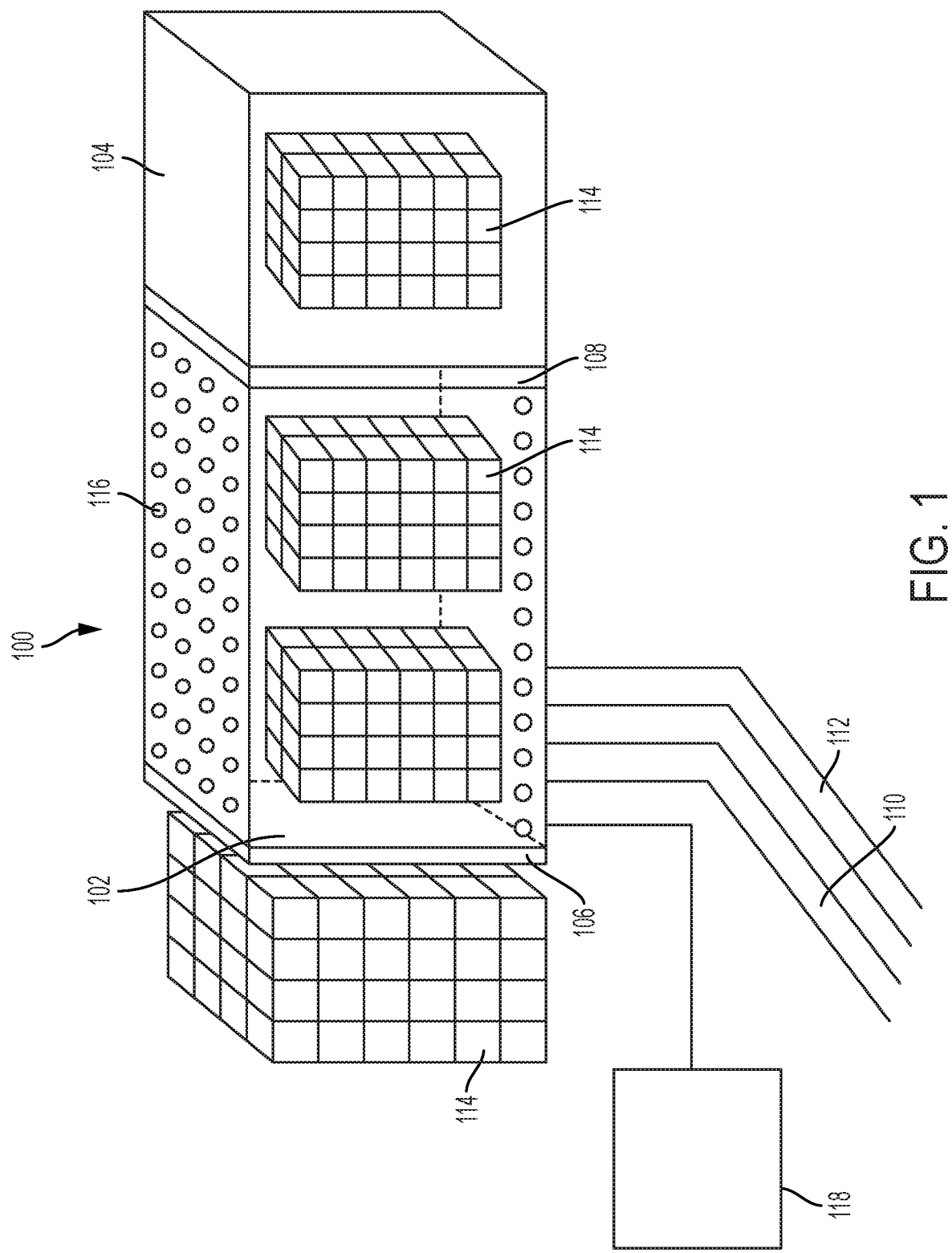
FIG. 1 is a schematic representation of an embodiment of a system for supercooling perishable products.
Figure 2:
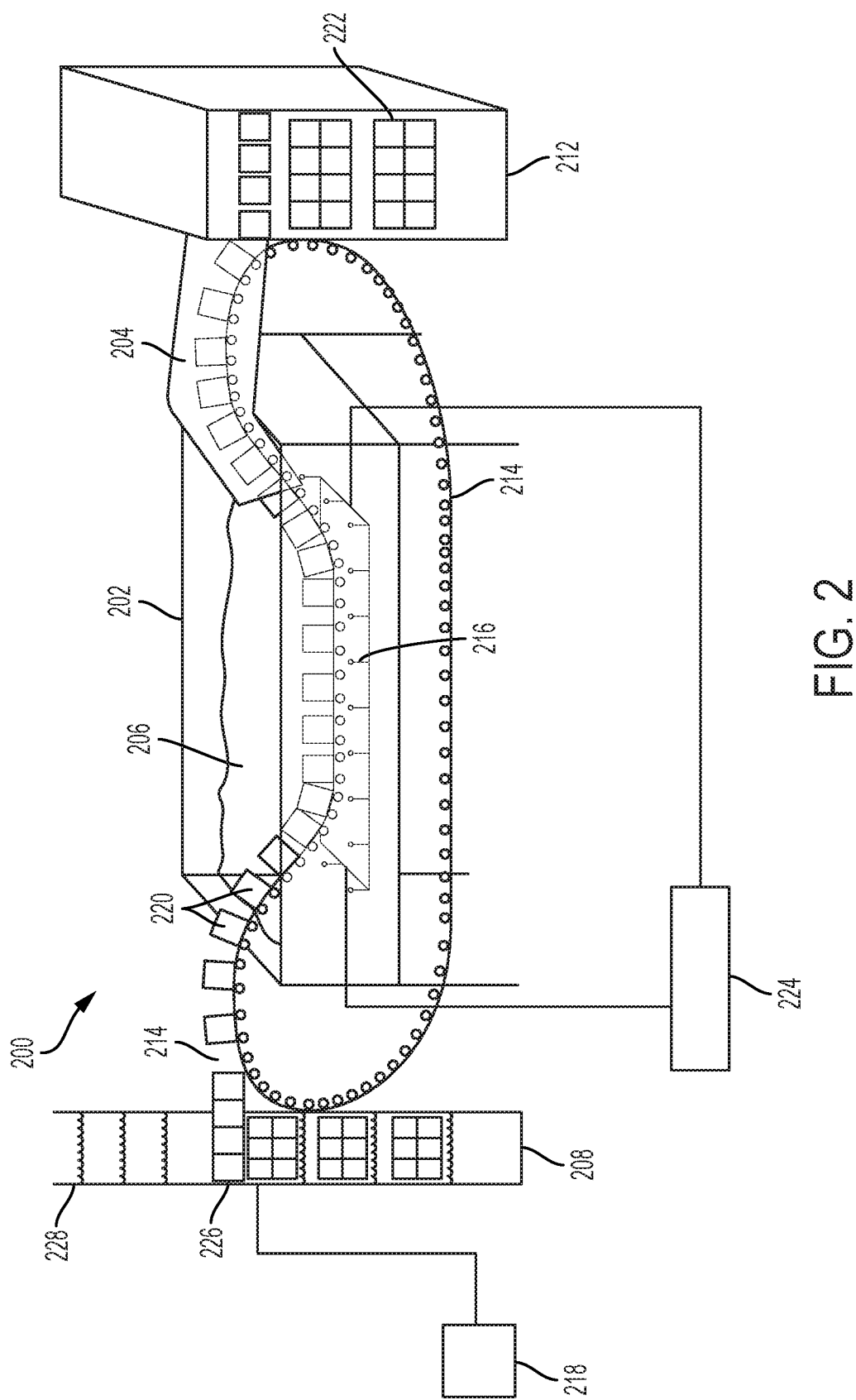
FIG. 2 is a schematic representation of another embodiment of a system for supercooling perishable products.

Referring generally to FIGS. 1 and 2, embodiments of a supercooling system are described. The supercooling systems 100 and 200 of the described embodiments may be used to supercool perishable products below freezing to improve shelf life and freshness of the products. Advantageously, the supercooling systems may include disruptors which emit sound pulses and/or waves to prevent the formation of ice crystals and impede the negative effects of low temperature cooling inside of the perishable products which would otherwise damage the cells and tissues of the perishable products. Additionally, the supercooling systems may cool the perishable products faster and with greater effect and through automated means to improve the efficiency and costs of cooling perishable products.

Referring now to FIG. 1, supercooling system 100 may generally comprise a cooling chamber 102 and a finishing chamber 104. Perishable product 114 may enter cooling chamber 102 through first seal door 106. Cooling chamber 102 can be any sealed enclosure or chamber which can contain the cooling medium and/or be made air tight using a silicon or gas tight seal. Cooling chamber 102 may be an adaptation of or similar to a "tube cooler" in appearance with mechanical doors on each end of the enclosure chamber to facilitate transfer and batch processing using supercooling gas, or similar to any enclosure strong enough to hold a heavy super cooled liquid or gas such a cubic shaped tank with entrance, transfer, and exit gates/doors through which the product is conveyed during the supercooling treatment.

A cooling (or supercooling) medium, such as a liquid or gas, may be introduced into cooling chamber 102 through inflow 101 thereby cooling perishable product 114 inside the cooling chamber. According to embodiments, a cooling liquid may be, for example, salt water. According to embodiments, the cooling liquid may be any liquid capable of being cooled below 0° C. without freezing. According to embodiments, a cooling liquid may be capable of enhancing the uniform energy transmission and transfer of the sound wave energy into the product. According to embodiments, a cooling gas may be air components such as $N_2$ or other gasses and blends. According to embodiments, the environment containing the supercooling atmosphere may also be refrigerated, under positive or negative pressure, or a cooled gas blend recirculated at a controlled temperature level, or it may include transitional cooling with $N_2$ liquid to gas in a gravity controlled conversion. Outflow 112 allows liquid or gas in cooling chamber 102 to be removed. Additionally, or alternatively, outflow 112 may be used to create a vacuum environment inside of cooling chamber 102.

Cooling chamber 102 may contain a plurality of disruptors 116. Disruptors 116 may emit pulses and/or sound waves at various frequencies during supercooling of perishable product 114. According to embodiments, disruptors may also emit electrical pulses or currents, or use controlled magnetic resonance. The energy of the emitted pulses and/or waves may be used to prevent and/or disrupt the formation of ice crystals that would otherwise form inside the perishable product 114 as the temperature inside cooling chamber 102 is brought to below freezing to reduce the possibility of cellular damage during the cooling process. Additionally or alternatively, the energy of the emitted pulses and/or waves may be used to target and terminate or disrupt the life cycle of some unwanted insects or other organisms that may be in or on the product. According to embodiments, careful control of the supercooling process and the energy level of the sound/ultrasound waves may negatively impact organisms such as resistant pests, spoilage organisms, pathogenic diseases, and live insects, even in a protected or dormant state such as spores, eggs, or cysts, with little or no damage to adjacent product tissue. Disruptors 116 may also contain a sensor to allow measurement as needed of temperature and/or to confirm/help provide feedback as to the frequency, volume, uniformity, and intensity of the sound/ultrasound waves in the environment containing the product. Cooling chamber 102 may include programmable controls 118 to control atmospheric composition, temperature, and frequency and emission pattern of disruptors 116. After cooling, perishable product 114 may be moved to finishing chamber 104 through second seal door 108. According to embodiments, a conveyor system may be integrated into the system, or a track with automatic and manual controls to move, for example, products, pallets of products, and bins. According to embodiments, and without limitation, perishable products may be prepackaged consumer products and/or bulk packaging, semi-rigid or flexible packages with or without atmospheres in packaging, semi-rigid flex-sides, pouches, semi-rigid bottles, and lidded containers.

According to embodiments, cooling chamber 102 is cooled to a temperature below freezing for a brief period of time until all metabolic activity is stopped or nearly stopped in perishable product 114. According to embodiments, the temperature of cooling chamber 102 may be, for example, −20° to 0° C. According to embodiments, the temperature of cooling chamber 102 may be, for example, −10° to −5° C. According to embodiments, perishable product 114 may be cooled in cooling chamber 102 for about 1 minute to about 60 minutes. According to embodiments, perishable product 114 may be cooled in cooling chamber 102 for about 1 minute to about 120 minutes. According to embodiments, disruptors 116 may emit sound pulses or waves at optimal frequencies that pass through perishable product 114 for disrupting crystals at targeted resonant frequency and preventing small ice crystal formation inside and on perishable product 114. According to embodiments, cooling chamber 102 may include an oscilloscope and/or voltmeter and/or variable oscillator connected to an amplifier and speaker to determine the target resonant frequency. According to embodiments, disruptors 116 may provide more than one resonance and may require an array and/or more complex targeting of the desired resonant frequency to accommodate perishable products 114 with complex geometries. According to embodiments, the direction and travel of the generated waves may be controlled for targeted disruption of ice crystal formation.

The temperature within finishing chamber 104 may be adjusted to an optimum safe holding temperature and environmental state for perishable product 114. For example, according to embodiments, the temperature inside finishing chamber 104 may slowly be warmed to a temperature above freezing. According to embodiments, the final warming temperature may be the temperature in which ice crystals/cell damage no longer occur, for example, from about −10° to about 20° C. According to embodiments, the final warming temperature may be −5° to about 5° C. According to embodiments, finishing chamber 104 may also contain a plurality of disruptors 116 that may emit pulses or waves during warming. The energy of the emitted pulses and/or waves prevents the formation of ice crystals that would otherwise form inside the perishable product 114 as the temperature inside warming chamber 104 is brought from below freezing to above freezing. According to embodiments, perishable product 114 may be warmed in finishing chamber 104 from about 1 second to about 20 minutes.

According to embodiments, perishable product 114 may be warmed in finishing chamber 104 from about 1 second to about 60 minutes.

The number and arrangement of disruptors 116 inside cooling chamber 102 and/or finishing chamber 104 is not limited. For example, according to an embodiment, at least one disruptor 116 is arranged on each internal surface of cooling chamber 102 and/or finishing chamber 104. According to an embodiment, the number and arrangement of disruptors 116 is the same in both cooling chamber 102 and finishing chamber 104. According to an embodiment, the number and arrangement of disruptors 116 in cooling chamber 102 is different from the number and arrangement of disruptors 116 in finishing chamber 104. According to embodiments, a plurality of disruptors 116 are arranged to form a complete surround sound system around perishable product 114. According to embodiments, the plurality of disruptors 116 can be programmed to create a customized sound program whereby each disruptor 116 emits a specified frequency at a specified time for a specified duration to optimally disrupt crystal and ice formation in perishable product 114. According to embodiments, the sound program may be the same or different in cooling chamber 102 and finishing chamber 104.

According to embodiments, perishable product 114 may be, for example, whole products, raw, cut, and partially processed products, drinks, juices, liquids, organic products, or any other perishable product in which the use of thermal treatment or microwaves would negatively affect the quality of the product. According to embodiments, and without limitation, perishable products may include fresh produce, seafood, meat, pressed juices, dairy, and ready to eat food items. According to an embodiment, perishable product 114 may be bulk packaged or stacked on pallets with or without wrapping. According to embodiments, perishable product 114 may be supercooled during prepackaging. According to embodiments, pre-packaging may be flexible or semi-flexible packaging with or without atmospheric pressure regulation.

According to embodiments, perishable products 114 may be manually moved into cooling chamber 102 and from cooling chamber 102 into finishing chamber 104. According to embodiments, supercooling system 100 may integrate an automatic conveyance system which allows for automatic progression of perishable product 114 from cooling chamber 102 to finishing chamber 104. According to embodiments, the cooling chamber 102 and/or finishing chamber 104 may have open tops to allow perishable product 114 to be lowered into the cooling chamber 102. According to embodiments, perishable product 114 may pass through from cooling chamber 102 to finish chamber 104 on a conveyor or via an overhead conveyor as needed with gates or doors between chambers.

According to embodiments, a single chamber may be utilized for both the cooling and warming, by first running a cooling cycle followed by a warming cycle. According to embodiments, cooling chamber and/or finishing chamber may be a tube cooler. According to embodiments, cooling and/or warming of perishable product 114 may be done under a vacuum.

According to embodiments, any liquid or gas utilized and not lost in the process can be recycled to a reservoir of liquid/gas as practical and economical. According to embodiments, supercooling system 100 may utilize conventional cooling methods without additional liquid, gas, atmospheric pressure regulation when cooling capabilities are sufficient to lower product temperatures to at or below the products freezing point and the environment is suitable for the use of sound and/or ultrasound waves to prevent ice crystals from forming and damage to the cellular structure of the product(s) being treated.

According to embodiments, disruptor 116 may include one or more piezoelectric transducers or piezoelectric crystals. According to embodiments, disruptor 116 may include an electric meter. According to embodiments, the system may include at least one of the following: transducer, multiplexer, transmitter and its beam-forming apparatus, transmit/receive (T/R) switches, low-noise amplifier, signal- and image-processing display, audio, A/D converter and its driver, the TGC (time-gain-compensation) amplifier. According to embodiments, the system may employ, for example, more than 200 channels.

Referring now to FIG. 2, an alternate embodiment is now described. Supercooling system 200 may include a continuous, automatic, conveyance system to automatically load perishable product 220 into cooling chamber 202, and convey from cooling chamber 202 to finishing chamber 204. In the finishing chamber 204, the now supercooled perishable product 222 may be further conveyed for stacking, bulk packaging, and/or transportation or storage. Perishable products 220 designated for supercooling may be loaded onto input feed 208 and may be automatically conveyed toward cooling chamber 202. Input feed 208 may be a moving belt. System feed 226 moves perishable product 220 onto conveyance system 214 for transport to cooling chamber 202. According to embodiments, the conveyance system may be, for example, a moving belt for carrying medium that rotates in a continuous loop along two or more pulleys, chain driven track or roller system of conveyance, or a PLC controlled magnetic track system. According to embodiments, the conveyance system may be an automated gravity track system that may carry the master shipping unit (plastic RPC or boxes). Cooling chamber 202 may contain supercooling fluid 206. Supercooling fluid 206 may be, for example, water with a food safe additive such as a mineral salt. Cooling chamber 202 may be completely or nearly completely enclosed to maintain its internal temperature and atmosphere, and/or to prevent the leakage of the supercooling fluid 206 to outside of cooling chamber 202. Cooling chamber 202 may be made of metal, ceramic, or other materials of sufficient strength and quality for the purpose, and the chamber may also be coated with a substance to help manage the caustic and echo effects within the chamber.

According to embodiments, supercooling system 200 may include integrated controls 218 to program the speed at which perishable product 220 is conveyed from input feed 208 towards conveyance system 214, and the speed at which perishable product 220 is conveyed along conveyance system 214, thereby controlling the time in which perishable product 220 remains in cooling chamber 202 and finishing chamber 204. According to embodiments, controls 218 may include PLU, computer, with accompanying drives. For example, the speed at which conveyance system 214 moves perishable product 220 may be programmed to allow for perishable product 220 to reach the optimum core supercooling temperature. According to embodiments, cooling time may be, for example 5 minutes to 60 minutes per batch. According to embodiments, cooling time may be, for example, 30-40 minutes per batch. According to embodiments, controls 218 may be programmed to control atmospheric composition and temperature of cooling chamber 202 and finishing chamber 204.

Cooling chamber 202 may contain a plurality of disruptors 216 that emit pulses or waves within cooling chamber 202. The energy of the emitted pulses and/or waves prevents the formation of ice crystals that would otherwise form inside the perishable product 220 as the temperature inside cooling chamber 202 is brought below freezing. Electric generator 224 may be circuited with disruptors 216. Disruptors 216 may emit pulses and/or sound waves at various frequencies during supercooling of perishable product 220. According to embodiments, disruptors 216 may include an array of transducers for ultrasound and "sound speakers" for low/lower frequency sounds that provide soundwaves. In some embodiments, these soundwaves may be pulses in bursts of a few cycles each time they get a short transmit pulse (similar to "ping and ring" in medical use). The excitation pulse amplitudes may be determined as to the order of magnitude. The magnitude of the pulse may determine the amount of energy beamed into the product.

In order to minimize distortion, embodiments may transmit additional types of pulses. These may be used to contrast, supplement, and better control the distorted spectrum of a broadband pulse after it is bounced around in the treatment medium (air, liquid, gas) and product. According to embodiments, disruptors 216 may also emit electrical pulses or currents, or use controlled magnetic resonance. Ultrasound waves can be produced using magnetism instead of electricity. According to embodiments, disruptors 216 may include magnetostrictive crystals and/or magnetostrictive transducers. Disruptor 216 may also contain a sensor. According to embodiments, controls 218 may be programmed to control the frequency and emission pattern of disruptors 216. According to embodiments, the audio signal from the transducer (microphone) may be passed through one or more processing units, which may prepare it for amplification. The signal may be fed to a recording device for storage. The stored signal may be played back and fed to more processors. The signal may be amplified and fed to a loudspeaker designed to optimize the sound waves directly at the product.

The number and arrangement of disruptors 216 inside cooling chamber 202 and/or finishing chamber 204 is not limited. For example, according to an embodiment, disruptors surround conveyance system 214 thereby surrounding perishable product 220 as it moves through cooling chamber 202. According to an embodiment, at least one disruptor 216 is arranged on each internal surface of cooling chamber 202 and/or finishing chamber 204. According to an embodiment, the number and arrangement of disruptors 216 is the same in both cooling chamber 202 and finishing chamber 204. According to an embodiment, the number and arrangement of disruptors 216 in cooling chamber 202 is different from the number and arrangement of disruptors 216 in finishing chamber 204. According to embodiments, a plurality of disruptors 216 are arranged to form a complete surround sound system around perishable product 220 or use targeted arrays of focused transducers and/or speakers to optimize the use of soundwaves for the intended purpose. According to embodiments, the plurality of disruptors 216 can be programmed to create a customized sound program whereby each disruptor 216 emits a specified frequency at a specified time for a specified duration to optimally disrupt crystal and ice formation in perishable product 220. Alternatively, the use of phased arrays similar to modern radar that allows the beam to be manipulated by varying the phase and power of the signal between antenna radiators, and the beam is swept around the sky without any moving parts, the same method can be used by ultrasound to sweep a beam of acoustic energy around the product(s). There may be programmed phase and amplitude shifts between the pulses of energy delivered to the piezoelectric elements arrayed in the transducer head. This will result in an incident beam of energy directed along a line into the product(s). The beam will be swept back and forth in the product(s) like the radar across the sky.

According to the embodiment of FIG. 2, conveyance system 214 may transport perishable product 220 from cooling chamber 202 to finishing chamber 204 upon the core temperature of perishable product 220 reaching below freezing. The temperature within finishing chamber 204 may be adjusted to an optimum safe holding temperature and environmental state for perishable product 220. For example, according to embodiments, the temperature inside finishing chamber 204 may be varied to be slowly warmed to a temperature above freezing. According to embodiments, the warming time may be from about 1 second to about 20 minutes. According to embodiments, finishing chamber 2014 may be warmed using controlled air temperature and air flow, and/or via atmospheric adjustment with or without a gas treatment (controlled air inflow with or without an industrial gas addition). According to embodiments, finishing chamber 204 may also contain a plurality of disruptors 216 that may emit pulses or waves during warming to prevent ice formation while perishable product 220 is slowly warmed to above freezing. In one embodiment, the ultrasound can warm the product.

According to the embodiment of FIG. 2, when perishable product 220 reaches an optimum temperature above freezing, conveyance system 214 transports the now supercooled perishable product 222 from finishing chamber 204 to output feed 212. Output feed may further transport supercooled perishable product 222 to other locations to be further processed, packaged, transported, or stored. According to embodiments, the products may be further packaged and/or shipped or stored as any other normal perishable product, but taking extra care not to allow the supercooled product to become warmer than optimal during the onward handling and distribution to customers/consumers. Other treatments to preserve, protect, and or enhance perishable products make occur in conjunction with the supercooling process.

According to the embodiment of FIG. 2, once supercooled perishable product 222 is released to output feed 212, the continuous belt of conveyance system 214 returns to input feed 208 to again transport perishable product 220 from system feed 226, thereby forming a loop. According to embodiments, conveyance system 214 may move at a constant speed. According to embodiments, conveyance system 214 may be programmed to move at varying speeds and/or to pause motion during particular points during the supercooling cycle. Conveyance system 214 may be programmed and controlled by controls 218.

According to embodiments, ambient air inside cooling chamber 202 may be removed by vacuum prior to injection of supercooling fluid 206. According to embodiments, supercooling fluid 206 may be a liquid or a gas. According to an embodiment, supercooling fluid 206 may be, for example, liquid $CO_2$, liquid nitrogen, or a combination. According to embodiments, supercooling may use any known method of cooling a product so long as during the cooling process when the temperature goes to or below the products freezing temperature (also in and around the product) and before the low temperature negatively affects the product (i.e. the point where ice crystals or damage may occur) sound/ultrasound/magnetic/gravitational waves must first be deployed to prevent product damage. According to embodiments, liquid $CO_2$ and/or liquid nitrogen may be vaporized and injected into cooling chamber 202. According to an embodiment, the vaporized $CO_2$ and/or nitrogen may be metered through sensors into cooling chamber 202. According to embodiments, controls 218 may be programmed to control the vacuum of air from cooling chamber 202 and the injection of supercooling fluid 206 into cooling chamber 202. According to embodiments, controls 218 may control the metering and sensing of supercooling fluid 206.

Other aspects of supercooling system 200 may be similar to those of the previously described embodiments. It is foreseen that the aspects and features of the various embodiments described herein may be used in combination with each other.

While various exemplary embodiments have been described above, it should be understood that they have been presented by way of example only, and not limitation. Thus, the breadth and scope of the present disclosure should not be limited by any of the above-described exemplary embodiments.

I claim:

1. A method for supercooling a product, the method comprising:
    surrounding a product in a supercooling medium until the product reaches an initial core temperature of from about −20° C. to about 0° C.;
    disrupting the formation of ice crystals within the product while in the supercooling medium using sound waves, ultrasound waves, electromagnetic waves, or combinations thereof while maintaining the initial core temperature; and
    warming the product from the initial core temperature to a warming temperature ranging from just below freezing to above freezing.

2. The method of claim 1, wherein the disrupting is by sound waves.

3. The method of claim 1, wherein the disrupting is by ultrasound waves.

4. The method claim 1, wherein the disrupting is by electromagnetic waves.

5. The method of claim 1, wherein the product is a perishable product.

6. The method of claim 1, wherein surrounding a product is by immersion.

7. The method of claim 1, wherein the supercooling medium comprises liquid $CO_2$ or N, gaseous $CO_2$ or N, or combinations thereof.

8. The method of claim 1, wherein the supercooling medium comprises cooled air.

9. The method of claim 1, wherein the immersing step takes from about 1 minute to about 120 minutes.

10. The method of claim 1, wherein the warming step further comprises disrupting the formation of ice crystals within the perishable product using sound waves.

11. The method of claim 1, wherein the warming temperature is from about −5° C. to about 20° C.

12. The method of claim 1, wherein the warming step takes from about 1 second to about 60 minutes.

13. A system for supercooling a product, the system comprising:
    a cooling chamber containing a supercooling medium;
    a warming chamber; and
    disruptors that emit waves, the disruptors located inside the warming chamber and the cooling chamber,
    wherein during a cooling cycle the chamber reaches a cooling temperature of from about −20° C. to about 0° C. and during a warming cycle the chamber reaches a warming temperature greater than the cooling temperature, wherein the cooling cycle is directly followed by the warming cycle.

14. The system of claim 13, wherein the waves are sound waves.

15. The system of claim 13, wherein the waves are ultrasound waves.

16. The system of claim 13, wherein the waves are electromagnetic waves.

17. The system of claim 13, wherein the product is a perishable product.

18. The system of claim 13, wherein the supercooling medium is chilled air.

19. The system of claim 13, wherein the supercooling medium comprises liquid $CO_2$ or N, gaseous $CO_2$ or N, or combinations thereof.

20. The system of claim 13, wherein the disruptors emit a frequency from about 20 Hz to about 300 GHz.

21. The system of claim 13, wherein a perishable product is immersed in the supercooling medium until the perishable product reaches a core temperature from about −20° C. to about 0° C.

22. The system of claim 13, further comprising:
    a conveyance system, wherein the conveyance system transports a perishable product from the cooling chamber to the warming chamber.

* * * * *